United States Patent
Kim et al.

(10) Patent No.: US 10,751,929 B2
(45) Date of Patent: Aug. 25, 2020

(54) MANUFACTURING DEVICE FOR MICRO-NEEDLE

(71) Applicant: RAPHAS Co., Ltd., Seoul (KR)

(72) Inventors: Hong Kee Kim, Gunpo-si (KR); Jung Dong Kim, Seoul (KR); Jung Hyun Bae, Seoul (KR); Yang Gi Lee, Seoul (KR); So Hyun Park, Incheon (KR); Do Hyeon Jeong, Seoul (KR)

(73) Assignee: RAPHAS CO., LTD., Seoul (KR)

( * ) Notice: Subject to any disclaimer, the term of this patent is extended or adjusted under 35 U.S.C. 154(b) by 419 days.

(21) Appl. No.: 15/248,354

(22) Filed: Aug. 26, 2016

(65) Prior Publication Data
US 2017/0190098 A1 Jul. 6, 2017

(30) Foreign Application Priority Data
Dec. 30, 2015 (KR) .................. 10-2015-0189855

(51) Int. Cl.
*B29C 55/00* (2006.01)
*B29C 33/30* (2006.01)
(Continued)

(52) U.S. Cl.
CPC ......... *B29C 55/00* (2013.01); *A61M 37/0015* (2013.01); *B29C 33/30* (2013.01);
(Continued)

(58) Field of Classification Search
CPC ...... A61M 2037/0053; A61M 37/0015; B29C 2037/90; B29C 33/30; B29C 37/00;
(Continued)

(56) References Cited

U.S. PATENT DOCUMENTS 3,981,671 A * 9/1976 Edwards ................. B29C 33/26
425/453
4,693,448 A * 9/1987 Proksa .................... B29C 33/24
100/214
(Continued)

FOREIGN PATENT DOCUMENTS

JP H11253869 A 9/1999
KR 20110012986 A 2/2011
(Continued)

*Primary Examiner* — Matthew J Daniels
*Assistant Examiner* — Yunju Kim
(74) *Attorney, Agent, or Firm* — Dinsmore & Shohl LLP; Yongsok Choi, Esq.

(57) ABSTRACT

A manufacturing device for a microneedle includes an upper plate stage, a lower plate stage disposed in horizontally parallel with the upper plate stage, a rotating device configured to rotate and move the upper plate stage over the lower plate stage, and a first cylindrical type actuator configured to vertically move the lower plate stage in a state in which the upper plate stage has been rotated and moved over the lower plate stage by the rotating device. The first cylindrical type actuator may upwardly and downwardly move so as to be able to stretch a viscous composition in a vertical direction in a state in which a contacting to the viscous composition is performed, wherein the viscous composition is applied on both of a patch sheet seated on the upper plate stage and a patch sheet seated on the lower plate stage, or is applied on one of them.

6 Claims, 4 Drawing Sheets

(51) Int. Cl.
  *B29C 37/00*   (2006.01)
  *A61M 37/00*   (2006.01)
  *B81C 1/00*    (2006.01)
  B29K 105/00    (2006.01)
  B29L 31/00     (2006.01)

(52) U.S. Cl.
  CPC ..... *B29C 37/00* (2013.01); *A61M 2037/0053* (2013.01); *B29C 2037/90* (2013.01); *B29K 2105/0058* (2013.01); *B29L 2031/7544* (2013.01)

(58) Field of Classification Search
  CPC . B29C 55/00; B29C 2043/3272; B29C 55/08; B29C 55/02; B29C 37/0025; B29C 43/361; B29C 2043/3283; B29C 5/00; B29C 35/08; B29C 33/24; B29K 2105/0058; B29L 2031/7544; B05D 5/00
  USPC .................. 425/171, 453; 156/60; 264/40.1
  See application file for complete search history.

(56) References Cited

U.S. PATENT DOCUMENTS

2005/0116370 A1\* 6/2005 Ogino .................. B82Y 10/00
                                                    264/40.1
2011/0240201 A1\* 10/2011 Jung ................ A61M 37/0015
                                                      156/60

FOREIGN PATENT DOCUMENTS

KR        20120029315 A    3/2012
KR          101285085 B1   7/2013

\* cited by examiner

PRIOR ART

US 10,751,929 B2

MANUFACTURING DEVICE FOR MICRO-NEEDLE

CROSS-REFERENCE TO RELATED APPLICATIONS

This application claim priority to Korean Patent Application No. 2015-0189855 filed on Dec. 30, 2015, the entire contents of which are hereby incorporated by reference.

BACKGROUND

1. Technical Field

The present disclosure relates to a manufacturing device for a microneedle.

2. Description of the Related Art

A microneedle is mainly manufactured with a molding method in the related art. A molding type manufacturing device for a microneedle is disclosed in, for example, Korean Patent Application Publication No. 10-2011-0012986, and the like.

However, when a microneedle is manufactured with the molding method, there is a problem in that the microneedle is damaged in the course of separating a product at which the microneedle is formed from a mold. Also, there is a problem in that strength of the microneedle manufactured with the molding method is relatively weak.

To address the problems of such a molding type manufacturing device for a microneedle, the present inventor filed a patent application of a manufacturing device for a microneedle, which manufactures a microneedle with a totally new method, as Korean Patent Application No. 10-2012-0029315. The manufacturing device for a microneedle disclosed in the patent application will be schematically described with reference to FIG. 1. Component names indicated by reference numerals used in FIG. 1 are as follows.

110: Horizontal Movement Stage; 130: Vertical Movement Stage; 121: Screw; 122: Nut; 300a: Air Blower; and g: Substrate.

A manufacturing device for a microneedle of the related art includes a horizontal movement stage 110 and a vertical movement stage 130. The horizontal movement stage 110 is connected to a driving source configured with a screw 121 and a nut 122 to be movably arranged in a linear direction, and it linearly moves between a first position shown as an imaginary line in FIG. 1 and a second position shown as a solid line in FIG. 1. The vertical movement stage 130 is connected to the driving source to be movably arranged in a vertical direction.

Such a manufacturing device for a microneedle of the related art forms a bottom layer, which is a basis of an applying of a viscous composition, through a spraying on a rigid substrate g manufactured with a ceramic or a metal, and applies the viscous composition on the bottom layer, and a problem regarding an aspect of stably fixing the substrate g, at the least, does not occur.

However, the invention disclosed in Korean Patent Application No. 10-2015-0174066 (Title of Invention: Manufacturing Method for Microstructure), which was newly invented and filed by the present inventor, forms a bottom layer at a patch sheet that was separately manufactured in advance, instead of forming the bottom layer by applying a viscous composition on the substrate g, thereby inputting such a patch sheet to a microneedle manufacturing process.

The patch sheet used in the above invention is shown in FIG. 2. A patch sheet 30 shown in FIG. 2 will be described as follows.

Firstly, a supporting layer 31 is provided as a component of the patch manufacturing sheet 30. The supporting layer 31 may be made of a material having superior moisture permeability and stretchability and blocking penetration of drugs and bioactive substances, and a film may be used, wherein the film may be configured with one or more materials selected among, for example, a paper, a non-woven fabric, a woven fabric, a natural or synthetic rubber, polyethylenes terephthalate, polyvinyl chloride, polypropylene, polyurethane, polystyrene, polycarbonate, polyethylenes terephthalate glycol, poly(ethylene-co-vinyl alcohol), polyethylene, polyester, and nylon.

An adhesive layer 32 is located on an upper surface of the supporting layer 31. An adhesive used in the adhesive layer 32 is configured with a pressure sensitive adhesive component that is pharmaceutically usable, and a hydrophilic or organic solvent material and the like may be used. As such an adhesive polymer material, an acrylate based resin including an acrylate polymer, a vinyl acetate-acrylate copolymer and the like, a copolymer resin including a polyisobutylene, polystyrene, or polybutadiene copolymer, a rosin based resin, a polyterpene resin, a petroleum based resin, a terpene phenol resin, a silicon polymer, and a natural or synthetic rubber, or a mixture thereof may be used. A single adhesive polymer material or two or more mixed adhesive polymer material may be used.

A peeling film 33 is formed on an upper surface of the adhesive layer 32. As shown in FIG. 2, if the peeling film 33 is attached to the adhesive layer 32 while a cutting plane line of an approximate double oval shape (not limited to this shape) is formed at the peeling film 33, a portion thereof at which the cutting plane line is formed to be separable from another portion of the peeling film 33, for example, a central small oval portion of the double oval may be easily separated.

If the providing of the patch manufacturing sheet 30 of the structure described above is a first procedure of the manufacturing process, the removing of the central oval portion of the peeling film 33 using the pre-formed cutting plane line thereof is a second procedure, and this second procedure corresponds to a second diagram from a left side of FIG. 2. When the central oval portion of the peeling film 33 is removed, a portion of the adhesive layer 32 corresponding to the removed central oval portion is exposed.

Next, a bottom layer 34 is covered on the exposed adhesive layer 32. The term of the bottom layer 34 is used as a meaning of a bottom at which a microstructure is formed. The bottom layer 34 is come into contact with an adhesive of the adhesive layer 32 to maintain a firm coupled state. The bottom layer 34 may be any film having a hydrophilic surface so as to allow a microstructure to be formed thereon. Preferably, the bottom layer 34 may be any film having a constant and uniform thickness and a hydrophilic group on a surface thereof. More preferably, the bottom layer 34 may be a hydrophilic polymer film having stretchability of a proper level so as to be tightly attached to a curved portion.

As described above, if the patch sheet 30 manufactured in advance could be applied to the manufacturing device for a microneedle of the related art, it is necessary to perform a procedure of mounting the patch sheet 30 on the vertical movement stage 130 in a manual method or an automatic method using a robot arm and the like so that there is a difficulty in flatly fixing the patch sheet 30 while performing the procedure of mounting the patch sheet 30 due to high flexibility of the patch sheet 30, which is caused by a non-rigid solid material thereof different from a rigid solid material of the substrate g of the related art.

Therefore, there is a need for a microneedle manufacturing device capable of attaining a firm and precise fixing of the patch sheet 30 while increasing productivity.

Further, in the manufacturing device for a microneedle of the related art of FIG. 1, inefficiency regarding an aspect of space application exists owing to a large movement range of the horizontal movement stage 110.

SUMMARY

An object of the present disclosure is directed to address the above described problems of the related art.

More particularly, an object of the present disclosure is directed to provide a manufacturing device for a microneedle, which is capable of attaining a strong fixing of a patch sheet and a precise position controlling.

Also, an object of the present disclosure is directed to provide a manufacturing device for a microneedle, which is capable of maximizing space application by reducing a movement range of a stage.

A representative configuration of the present disclosure for attaining the objects is as follows.

A manufacturing device for a microneedle according to one embodiment of the present disclosure includes an upper plate stage, a lower plate stage disposed in horizontally parallel with the upper plate stage, a rotating device configured to rotate and move the upper plate stage over the lower plate stage, and a first cylindrical type actuator configured to vertically move the lower plate stage in a state in which the upper plate stage has been rotated and moved over the lower plate stage by means of the rotating device.

The first cylindrical type actuator may upwardly and downwardly move so as to be able to stretch a viscous composition in a vertical direction in a state in which a contacting to the viscous composition is performed, wherein the viscous composition is applied on both of a patch sheet seated on the upper plate stage and a patch sheet seated on the lower plate stage, or is applied on one of both of them.

Also, the manufacturing device for a microneedle according to one embodiment of the present disclosure may include a second cylindrical type actuator configured to vertically move the upper plate stage so as to contact to the viscous composition applied on both of a patch sheet seated on the upper plate stage and a patch sheet seated on the lower plate stage, or applied on one of both of them in a state in which the upper plate stage has been rotated and moved over the lower plate stage.

In addition, the manufacturing device for a microneedle according to one embodiment of the present disclosure may further include a monitoring device configured to inspect a position of the patch sheet seated on each of the upper plate stage and the lower plate stage. In this case, the monitoring device may sense whether or not a position indicator formed at the patch sheet and a position indicator formed at each of the upper plate stage and the lower plate stage are mutually corresponded to each other through an image, thereby outputting the sensed result. Meanwhile, the position indicator formed at the patch sheet may be formed as a hole at upper and lower parts of the patch sheet, and the hole may be used for a passing of a bar which is used for storing the patch sheet in a vertical direction.

Further, the manufacturing device for a microneedle according to one embodiment of the present disclosure may further include a vacuum absorber configured to fix a position of the patch sheet seated on each of the upper plate stage and the lower plate stage, wherein the vacuum absorber may fix the position of the patch sheet through a vacuum suction according to the sensed result representing that a position selection of the patch sheet has been exactly made output from the monitoring device.

In addition to the above described, other components may be further included in the manufacturing device for a microneedle according to the present disclosure According to the present disclosure, the problems, which have been described in Background, of the related art are solved.

More particularly, according to the present disclosure, it is provided a manufacturing device for a microneedle, which is capable of attaining a strong fixing of a patch sheet and a precise position controlling.

Also, according to the present disclosure, it is provided a manufacturing device for a microneedle, which is capable of maximizing space application by reducing a movement range of a stage.

BRIEF DESCRIPTION OF DRAWINGS

The above and other objects, features and advantages of the present disclosure will become more apparent to those skilled in the art by describing in detail exemplary embodiments thereof with reference to the accompanying drawings, in which.

DETAILED DESCRIPTION

Figure 1:
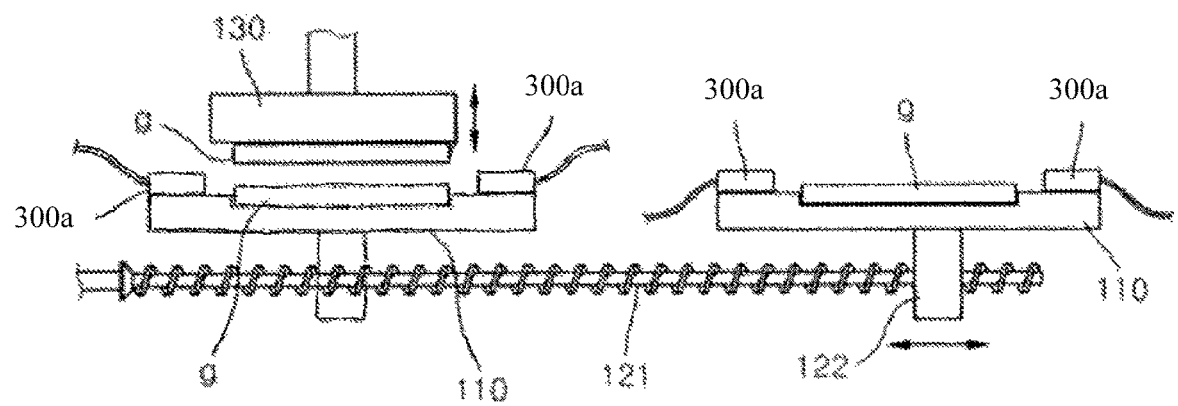
FIG. 1 is a diagram illustrating a manufacturing device for a microneedle of the related art.

The following detailed description with respect to the present disclosure will be described with reference to the accompanying drawings illustrating as examples of specific embodiments which can implement the present disclosure. These embodiments will be fully described in detail for allowing a person skilled in the art to implement the present disclosure. It should be understood that various embodiments of the present disclosure are different from each other, but they are not to be exclusive mutually. For example, specific shapes, structures, and features disclosed herein may be implemented by another embodiment in association with one embodiment without departing from the spirit and scope of the present invention. Also, it should be understood that positions and arrangements of respective components disclosed in each embodiment may be modified without departing from the spirit and scope of the present disclosure. The detailed description to be disclosed later, therefore, is not to be taken in a sense for limiting the scope of the present disclosure but for explanation thereof, and the scope of the present disclosure should be construed by the appended claims, along with the full range of equivalents to which such claims are entitled. In giving reference numerals to components of the drawings, the same or similar reference numerals are given to components having the same or similar functions throughout various aspects.

Hereinafter, for easily implementing the present disclosure by those skilled in the art, various preferable embodiments of the present disclosure will be described in detail with reference to the accompanying drawings.

Figure 3:
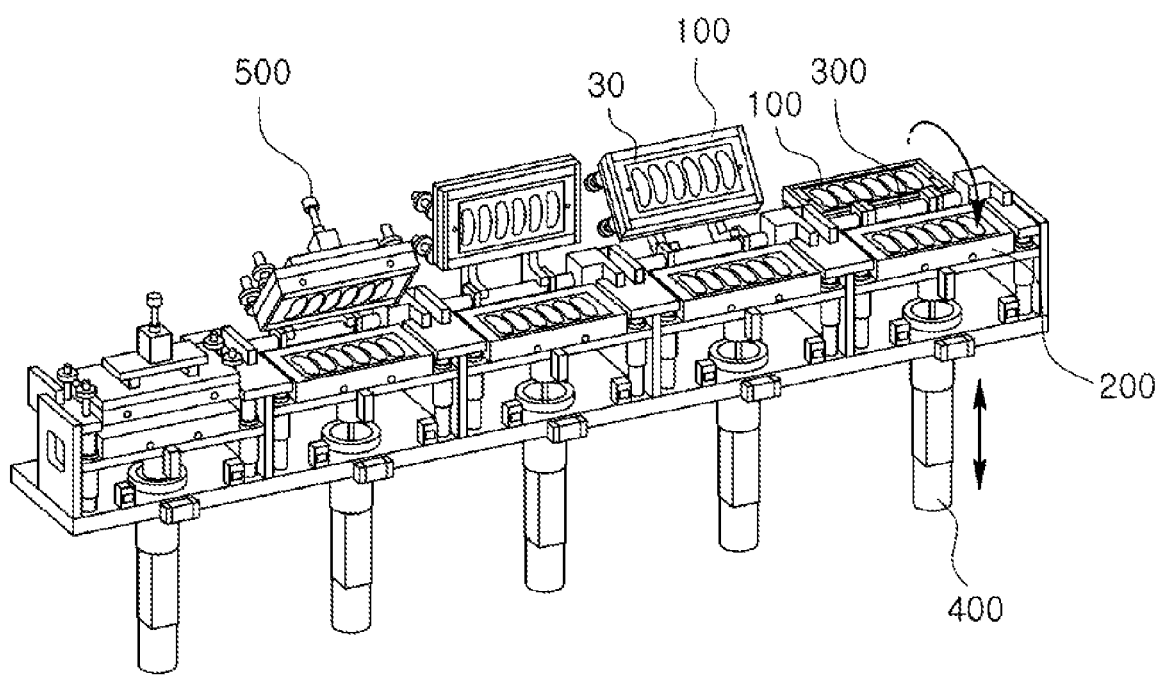
FIG. 3 is a diagram illustrating a manufacturing device for a microneedle according to the present disclosure.

A manufacturing device for a microneedle is shown in FIG. 3. More precisely, FIG. 3 shows a growing device that is the gist improvement in the present disclosure of an entire manufacturing device for a microneedle. In FIG. 3, a reference numeral 100 indicates an upper plate stage, a reference numeral 200 indicates a lower plate stage, a reference numeral 300 indicates a rotating device, a reference numeral 400 indicates a first cylindrical type actuator, and a reference numeral 500 indicates a second cylindrical type actuator.

As shown in FIG. 3, the upper plate stage 100 and the lower plate stage 200 are disposed in horizontally parallel with each other by interposing the rotating device 300. A combination of the upper plate stage 100 and the lower plate stage 200, which are disposed in horizontally parallel with each other by interposing the rotating device 300, may be provided by only one pair, whereas a plurality of pairs may be provided as shown in FIG. 3.

The patch sheet 30, on which a spraying of a viscous composition has been completed in a previous process, is seated on the upper plate stage 100 and the lower plate stage 200. The spraying of the viscous composition is performed by means of a dispenser that is not shown in FIG. 3.

The viscous material may include hyaluronic acid or its salt, polyvinylpyrrolidone, polyvinyl alcohol, cellulose polymer, dextran, gelatin, glycerine, polyethylene glycol, polysorbate, propylene glycol, povidone, carbomer, gum ghatti, guar gum, glucomannan, glucosamine, dammar gum, rennet casein, locust bean gum, microfibrillated cellulose, psyllium seed gum, xanthan gum, arabino galactan, arabic gum, alginic acid, gelatin, gellan gum, carrageenan, karaya gum, curdlan, chitosan, chitin, tara gum, tamarind gum, tragacanth gum, furcelleran, pectin, pullulan and the like.

More preferably, the viscous material used in the present disclosure may be hydroxypropyl methylcellulose, hydroxyalkyl cellulose, ethyl hydroxyethylcellulose, alkyl cellulose, and carboxymethyl cellulose. Most preferably, the viscous material used in the present disclosure may be carboxymethyl cellulose.

Also, the solvent for dissolving the viscous material is not specifically limited, and water, absolute or hydrous lower alcohol containing between 1 and 4 carbon atoms, acetone, ethyl acetate, chloroform, 1,3-butylene glycol, hexane, diethyl ether, or butyl acetate may be used as the solvent, and preferably, water or lower alcohol may be used as the solvent, and most preferably, water may be used as the solvent.

Such a spraying of the viscous composition may be performed to both of the patch sheet 30 seated on the upper plate stage 100 and the patch sheet 30 seated on the lower plate stage 200, or may be performed to one of both of them.

One of the gist improvements in the manufacturing device for a microneedle according to the present disclosure is that the upper plate stage 100 is rotated and moved over the lower plate stage 200 by means of the rotating device 300 in a state in which the patch sheet 30 is seated on both of the upper plate stage 100 and the lower plate stage 200. Such a rotational movement is shown as an arrow in FIG. 3. At a left-most stage among five pairs of stages shown in FIG. 3, a rotational movement of the upper stage 100 by means of the rotating device 300 has been completely performed. At second, third, and fourth stages from the left side, a rotational movement of each of the upper stages 100 by means of the rotating device 300 is gradually performed. At a right-most stage among the five pairs of stages shown in FIG. 3, a rotational movement of the upper stage 100 by means of the rotating device 300 is not absolutely performed.

It is apparent that the upper plate stage 100 is rotatably coupled to the rotating device 300 for the purpose of the rotational movement of the upper plate stage 100 as shown in FIG. 3. On the other hand, the lower plate stage 200 is not drive-coupled to the rotating device 300.

In a state in which the rotational movement of the upper plate stage 100 over the lower stage 200 has been completed, a contacting with respect to the viscous composition, which is applied on both of the patch sheet 30 seated on the upper plate stage 100 and the patch sheet 30 seated on the lower plate stage 200, or is applied on one of both of them, is performed. Subsequently, a stretching process is commenced. Such a stretching process is performed by means of the first cylindrical type actuator 400 shown in FIG. 3.

Another one of the gist improvements of the present disclosure is that the lower plate stage 200 is downwardly moved in a vertical direction to stretch the viscous composition, unlike the manufacturing device for a microneedle of the related art shown in FIG. 1 in which the upper plate stage 100 is upwardly moved in the vertical direction to stretch the viscous composition. In the stretching process being subsequently performed after the contacting of the viscous composition, a very fine controlling of a stretching speed and a stretched length may be necessary and quality of the microneedle that is a final product may be varied depending on how much a fine controlling is performed. Under such a circumstance, as compared to a controlling of the stretching speed and the stretched length while moving upwardly the stage that is a heavy thing, a controlling thereof while moving downwardly the stage may be advantageous regarding an aspect of accuracy of the controlling.

At the left-most stage in FIG. 3, a downward movement of the first cylindrical type actuator 400 has been terminated and thus the stretching with respect to the viscous composition has been terminated. At the remaining stages, because each of the upper plate stages 100 is in a state prior to a completion of a rotational movement over the lower plate stage 200 by means of the rotating device 300, a contacting with respect to the viscous composition is not performed, and thus a downward movement of the first cylindrical type actuator 400 is not performed so that it can be seen that a position of the first cylindrical type actuator 400 is different from that of the left-most stage.

In a state in which the rotational movement of the upper plate stage 100 over the lower plate stage 200 has been completed, when a contacting with respect to the viscous composition, which is applied on both of the patch sheet 30 seated on the upper plate stage 100 and the patch sheet 30 seated on the lower stage 200, or is applied on one of both of them, is exactly performed, the stretching process may be immediately performed by separating the upper plate stage 100 and the lower plate stage 200 from each other by a vertical direction distance, and the manufacturing device for a microneedle according to the present disclosure includes such an embodiment as the scope of the present disclosure. However, for an exact contacting to the viscous composition being applied, a very fine spacing between the upper plate stage 100 and the lower plate stage 200 should be remained when performing the rotational movement of the upper plate stage 100 over the lower plate stage 200 and completing the rotational movement. By considering a weight of the stage and inertia according to the rotational movement, such a controlling is very difficult although it is not impossible. For the purpose of such a precise degree of accuracy in the controlling, there may occur a problem in that cost is excessively required for the rotating device 300 itself and a controller therefor. Also, when the controlling is failure, the upper plate stage 100 may collide with the lower plate stage 200 and squash the viscous composition being applied, thereby causing occurrence of defects.

In consideration of the above described, the second cylindrical type actuator 500 may be included in the manufacturing device for a microneedle according to the present disclosure. As shown in FIG. 3, the second cylindrical type actuator 500 is drive-coupled to the upper plate stage 100. In the embodiment of providing such a second cylindrical type actuator 500, when the rotational movement of the upper plate stage 100 over the lower plate stage 200 is performed and the operation is terminated, a sufficient spacing may be provided between the upper plate stage 100 and the lower plate stage 200. As a result, the upper plate stage 100 is prevented in advance from colliding with the lower plate stage 200. As such, when the rotational movement operation is terminated while the sufficient spacing is provided between the upper plate stage 100 and the lower plate stage 200, an operation of the second cylindrical type actuator 500 is commenced. The second cylindrical type actuator 500 gradually reduces the spacing between the upper plate stage 100 and the lower plate stage 200 through the downward movement of the upper plate stage 100, thereby attaining the exact contacting with respect to the viscous composition.

Yet another one of the gist improvements of the present disclosure is that a monitoring device may be further included to inspect a position of the patch sheet 30 seated on each of the upper plate stage 100 and the lower plate stage 200. The transferring and the seating of the patch sheet 30 toward the manufacturing device for a microneedle shown in FIG. 3, more precisely, toward the growing stage may be performed by a manual process or an automatic process using a robot arm. If the seating of the patch sheet is not performed at exact positions on the upper plate stage 100 and the lower plate stage 200 by means of any one of the above described processes, the microneedle may not be formed at a desired position of the patch sheet so that a defect may occur.

Figure 2:
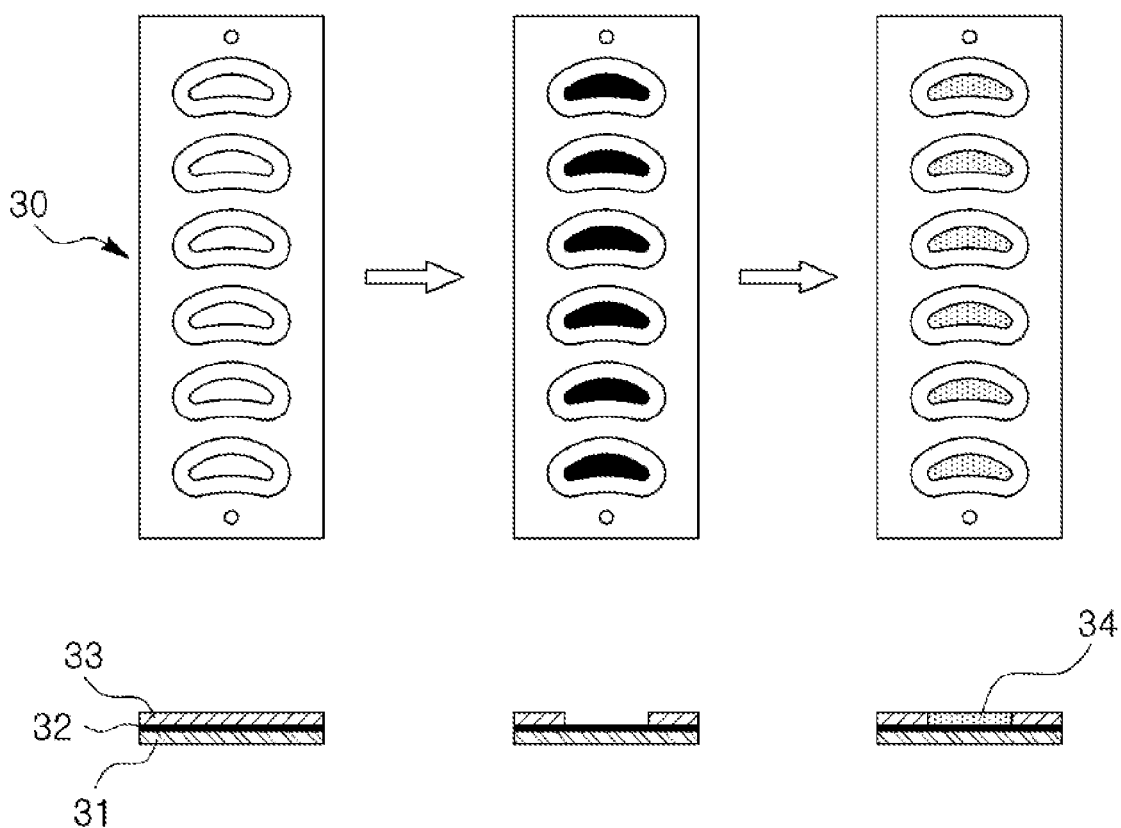
FIG. 2 is a diagram illustrating a patch sheet provided to a manufacturing device for a microneedle of the present disclosure.

The monitoring device, which is provided to prevent such a defect and to inspect the position of the patch sheet 30 seated on each of the upper plate stage 100 and the lower plate stage 200, may be implemented to sense whether or not position indicators formed at the patch sheet 30 and the upper and the lower plate stages 100 and 200 match with each other through an image, thereby outputting the sensed result. At this point, the position indicator formed at the patch sheet 30 may be formed as a hole at upper and lower parts of the patch sheet 30. Such a hole can be seen at each of the upper and lower parts of the patch sheet shown in FIG. 2. A hole may be formed at the upper plate stage 100 and the lower plate stage 200 so as to correspond to the position indicator of a hole shape formed at the patch sheet 30. A camera (not shown), which is a component of a monitoring system, photographs a mutual position relationship between the hole formed at the patch sheet 30 and the holes formed at the upper plate stage 100 and the lower plate stage 200. The photographed images regarding mutually overlapped holes are differently recognized in states in which an exact seating of the patch sheet 30 is performed or not, and thus an exact monitoring may be possible using such a recognition.

Figure 4:
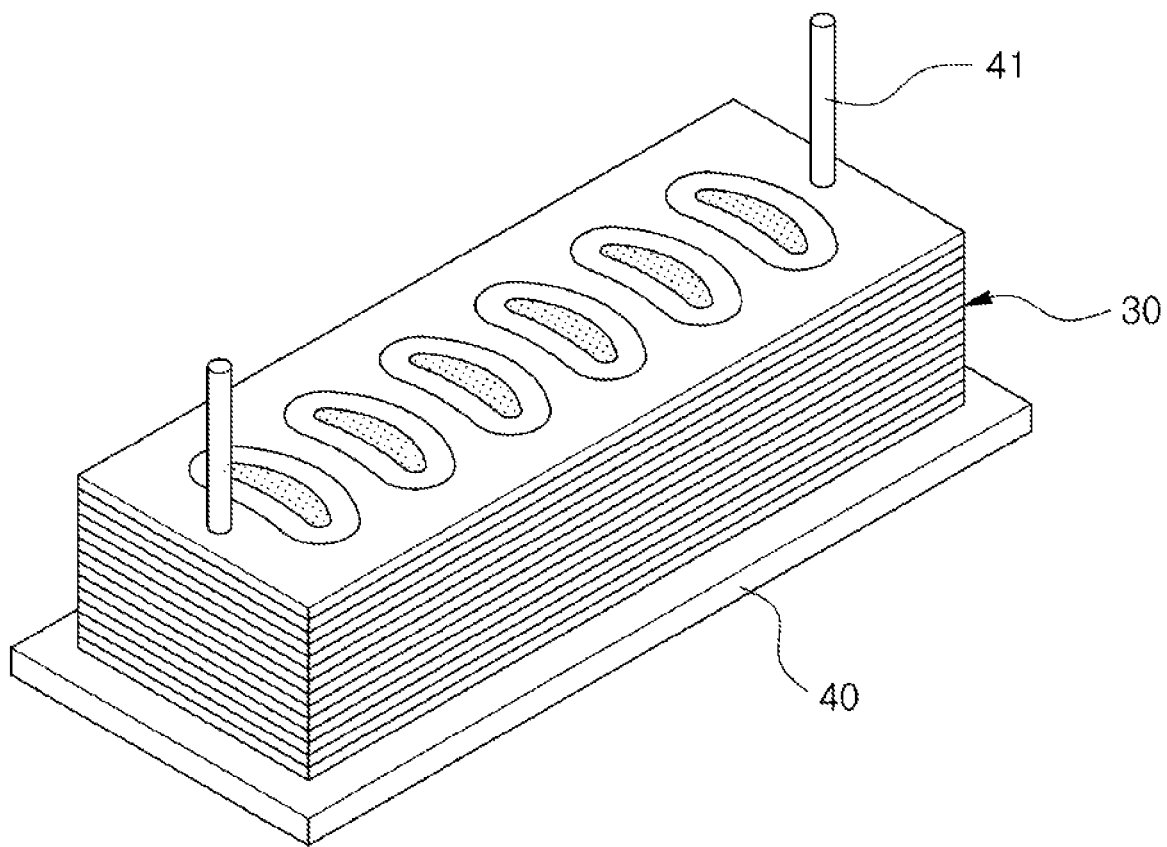
FIG. 4 is a diagram illustrating a state in which the patch sheet provided to the manufacturing device for a microneedle of the present disclosure is stored prior to an inputting to a process.

An additional advantage is attained by forming the position indicator, which is formed at the patch sheet 30, as a hole. This can be understood with reference to FIG. 4. FIG. 4 shows a state in which a bar 41 is fit into the hole functioning as the position indicator that is provided by one at each of the upper and lower parts of the patch sheet 30 so that a plurality of patch sheets 30 are stored on a sheet storing sheet 40 in a stacked manner. The plurality of patch sheets 30 in a state of waiting for being input to a microneedle manufacturing process are shown in FIG. 4. When the plurality of patch sheets 30 are provided to the microneedle manufacturing process in such a state, the individual patch sheet 30 is upwardly moved while being guided along the bars 41 through the holes formed at the upper and lower parts of the individual patch sheet 30 to thereby be escaped from the stored state as the robot arm having, for example, a vacuum absorber, moves downwardly and vacuum suctions an upper surface of the stored patch sheet 30 to upwardly move it.

In summary, by providing the patch sheet 30 with the position indicator in the form of a hole, there may be advantageous effects in that the patch sheet 30 may be exactly seated on each of the upper plate stage 100 and the lower plate stage 200 through a visual monitoring, and also the hole may be used as a through hole of the bar 41 so as to stack and store the patch sheets 30 in a standby state prior to an inputting to the process.

Subsequent to the monitoring of a seated position as described above, there may need to exactly fix the seated position. For this purpose, the manufacturing device for a microneedle according to the present disclosure may include a vacuum absorber. According to the result representing that a position selection of the patch sheet 30 has been exactly made output from the monitoring device which may be implemented as described above, the vacuum absorber may fix a position of the patch sheet 30 through a vacuum suction, thereby preventing movement of the patch sheet 30 while the upper plate stage 100 is rotationally moved by means of the rotating device 300, the lower plate state 200 is vertically moved by means of the first cylindrical type actuator 400, and the like.

As described above, it has been described for the visual monitoring method using the hole formed at the patch sheet 30 in the manufacturing device for a microneedle according to the present disclosure, but it should be understood that the scope of the present disclosure is not limited thereto. In the manufacturing device for a microneedle according to the present disclosure, it may not be necessary that the monitoring of the seated position should be performed. For example, an alignment of the patch sheet 30 may be performed with a method in which a protrusion formed at each of the upper plate stage 100 and the lower plate stage 200 is inserted into the hole formed at the patch sheet 30. Similarly, in the manufacturing device for a microneedle according to the present disclosure, the fixing of the seated position of the patch sheet 30 may be implemented by another method, for example, a latch fixing method, in addition to the vacuum suction method.

What is claimed is:
1. A system for manufacturing a microneedle, comprising:
   a first patch sheet including a first viscous composition applied on the first patch sheet;
   a second patch sheet including a second viscous composition applied on the second patch sheet:
   a manufacturing device comprising:
      an upper plate stage holding the first patch sheet;

a lower plate stage disposed in horizontally parallel with the upper plate stage and holding the second patch sheet;

a rotating device configured to rotate and move the upper plate stage over the lower plate stage;

a first cylindrical type actuator configured to vertically move the lower plate stage; and a second cylindrical type actuator positioned parallel to a vertical axis and configured to vertically move the upper plate stage until the first viscous composition of the first patch sheet come into contact with the second viscous composition of the second patch sheet, wherein the first cylindrical type actuator vertically moves the lower plate stage to stretch the first viscous composition and the second viscous composition to obtain the microneedle.

2. The system of claim 1, wherein the manufacturing device further comprises:

a monitoring device configured to inspect a position of the patch sheet seated on each of the upper plate stage and the lower plate stage.

3. The system of claim 2, wherein the monitoring device senses whether or not a position indicator formed at the patch sheet and a position indicator formed at each of the upper plate stage and the lower plate stage are mutually corresponded to each other through an image, thereby outputting a sensed result.

4. The system of claim 3, wherein the position indicator formed at the patch sheet is formed in a form of a hole at upper and lower parts of the patch sheet, and the hole is used for a passing of a bar which is used for storing the patch sheet in a vertical direction.

5. The system of claim 2, wherein the manufacturing device further comprises:

a vacuum absorber configured to fix a position of the patch sheet seated on each of the upper plate stage and the lower plate stage, wherein the vacuum absorber fixes the position of the patch sheet through a vacuum suction according to the sensed result representing that a position selection of the patch sheet has been exactly made output from the monitoring device.

6. The system of claim 1, wherein the patch sheet comprises a supporting layer, an adhesive layer forming on an upper surface of the supporting layer, and a peeling film forming on the adhesive layer.

* * * * *